United States Patent
Kateman

(10) Patent No.: US 10,278,578 B2
(45) Date of Patent: May 7, 2019

(54) SYSTEM AND METHODS FOR PROMOTING EYE CONTACT IN CHILDREN WITH AUTISM SPECTRUM DISORDER

(71) Applicant: Russell Kateman, Staten Island, NY (US)

(72) Inventor: Russell Kateman, Staten Island, NY (US)

( * ) Notice: Subject to any disclaimer, the term of this patent is extended or adjusted under 35 U.S.C. 154(b) by 118 days.

(21) Appl. No.: 15/703,831

(22) Filed: Sep. 13, 2017

(65) Prior Publication Data
US 2019/0076018 A1 Mar. 14, 2019

(51) Int. Cl.
A61B 5/16 (2006.01)
A61B 3/125 (2006.01)
A61B 3/00 (2006.01)
A61B 5/11 (2006.01)
A61B 5/00 (2006.01)

(52) U.S. Cl.
CPC .............. *A61B 3/125* (2013.01); *A61B 3/005* (2013.01); *A61B 5/1118* (2013.01); *A61B 5/168* (2013.01); *A61B 5/4833* (2013.01)

(58) Field of Classification Search
CPC ....... A61B 3/005; A61B 5/1118; A61B 5/168; A61B 5/4833
See application file for complete search history.

*Primary Examiner* — Jack Dinh

(57) ABSTRACT

A therapeutic methodology for improving eye contact in children with ASD. A plurality of pairs of contact lenses is provided to an adult, typically a therapist or a parent of a child, where the contact lenses have an image of a subject of interest to the child imprinted on the contact lens. The plurality of the pairs of contact lenses provides a series of pairs of contact lenses where the image is gradually faded. An adult interacting with the child begins by wearing contact lenses having an image of greatest intensity. Through a series of therapy sessions with the therapist uses the contact lenses, as the child's duration and frequency of eye contact improves, the therapist will then use lenses with the image of the subject of interest to the child that are gradually faded. When therapeutic goal of the targeted duration and frequency of eye contact is reached, therapy using the contact lenses can be terminated.

1 Claim, 3 Drawing Sheets

SYSTEM AND METHODS FOR PROMOTING EYE CONTACT IN CHILDREN WITH AUTISM SPECTRUM DISORDER

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

FIELD

At least some embodiments disclosed herein relate, in general, to the treatment of autism spectrum disorder and more specifically to autism spectrum disorder using specialized contact lenses configure to promote eye contact.

BACKGROUND

Autism is a pervasive developmental disorder characterized by difficulties in social interaction, verbal and non-verbal communication and repetitive behaviors, and occurs in 1 out of 68 children in the United States.

A well-known characteristic of autism spectrum disorder (ASD) is decreased eye contact. Behavioral studies have found that ASD individuals have impairments in face recognition and discrimination6-8 Eye tracking techniques have been used to examine how ASD individuals scan faces. Overall, existing studies have consistently found that ASD children and adults show reduced visual attention to faces compared to their typically developing (TD) counterparts. More specifically, Yi et al., found that ASD children's scanning differed significantly from that of the TD group only in the area of the eyes. The authors concluded that the face scanning abnormality in ASD children is limited only to the eye region, likely due to their strong tendency to avoid eye contact.

These eye contact abnormalities have been implicated as one factor interfering with social interaction for young children with ASD. In early development, eye contact serves to regulate face-to-face social interactionsll and contribute communicatively to social interactions. Later, eye contact responses coordinate the visual attention between another individual and an object of interest and have been found to be an influencing variable in language acquisition. It has also been suggestive that poor eye contact may adversely affect educational gain due to the relationship between eye contact and attending to the teacher.

Given the high prevalence of autism and the negative consequences of poor eye contact, a number of treatment options have been proposed including behavioral, pharmacological, and technological treatment options. Perhaps the most widely used and researched approach is referred to as applied behavioral analysis. Since the early 1960's applied behavior analysis (ABA) has been used by therapists to teach communication and social behavior to children with autism. We hypothesize that the combination of the contact lenses and ABA treatment will be more effective because the contact lens will be customized to the child's interest.

SUMMARY

In an embodiment, the present disclosure relates to a therapeutic methodology for improving eye contact in children with ASD. A plurality of pairs of contact lenses is provided to an adult, typically a therapist or a parent of a child, where the contact lenses have an image of a subject of interest to the child imprinted on the contact lens.

In an embodiment, the plurality of the pairs of contact lenses provides a series of pairs of contact lenses where the image is gradually faded. An adult interacting with the child begins by wearing contact lenses having an image of greatest intensity. Through a series of therapy sessions with the therapist uses the contact lenses, as the child's duration and frequency of eye contact improves, the therapist will then use lenses with the image of the subject of interest to the child that are gradually faded. When therapeutic goal of the targeted duration and frequency of eye contact is reached, therapy using the contact lenses can be terminated.

BRIEF DESCRIPTION OF THE DRAWINGS

The embodiments are illustrated by way of example and not limitation in the figures of the accompanying drawings in which like references indicate similar elements.

DETAILED DESCRIPTION

The following description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Figure 1:
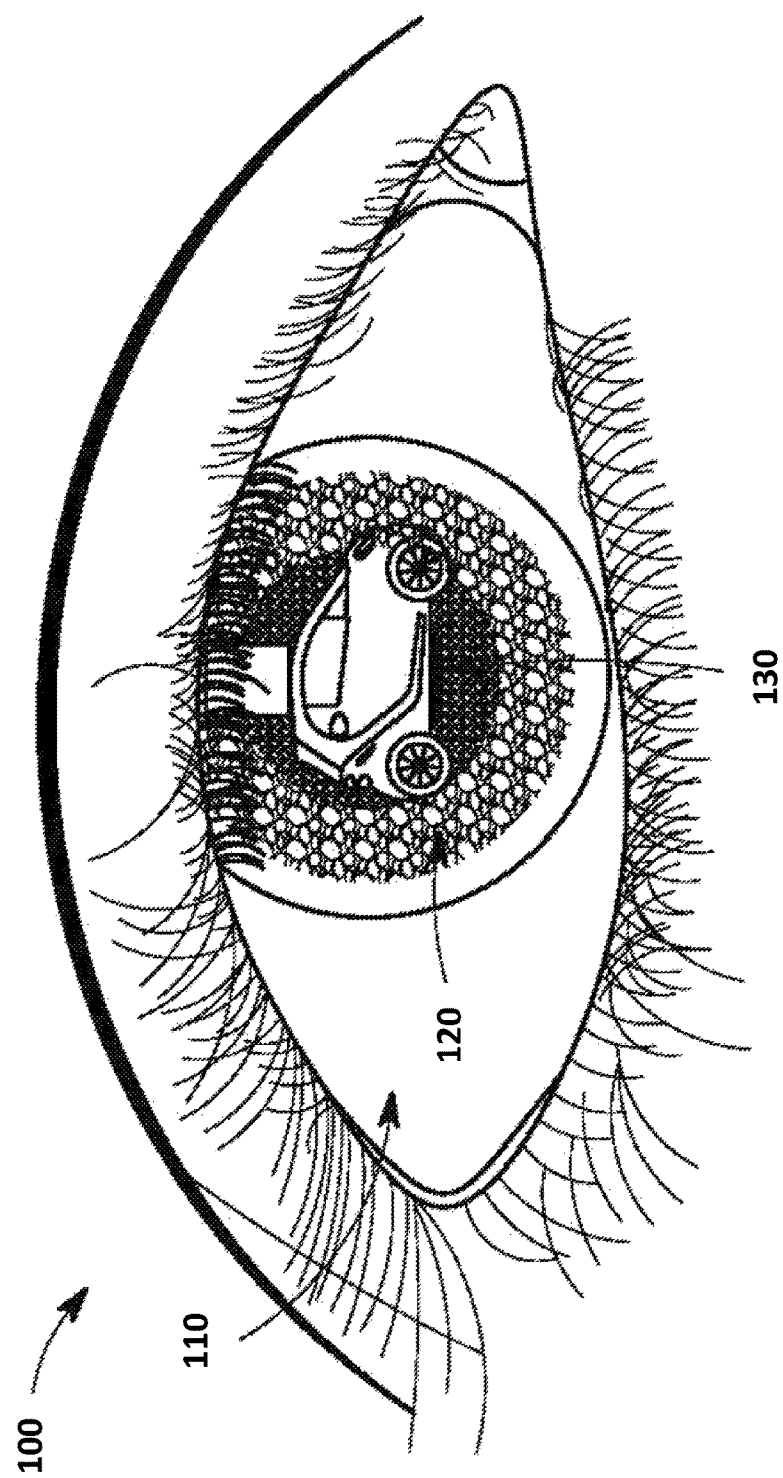
FIG. 1 illustrates an embodiment of a contact lens in accordance with the present disclosure.

The present disclosure relates to systems and methods for promoting eye contact in children with autism spectrum disorders. In an embodiment, the systems and methods utilize a set of disposable contact lenses that are imprinted with a subject of interest to a child, for example trucks. The contact lenses have two or more subsets, where a specific subset shows the subject of interest at a degree of intensity, and different subsets have different intensities. FIG. 1 show an example 100 of an eye 110 of a person wearing such a contact lens 120, where the lens is imprinted with an image of a truck 130.

Figure 2:
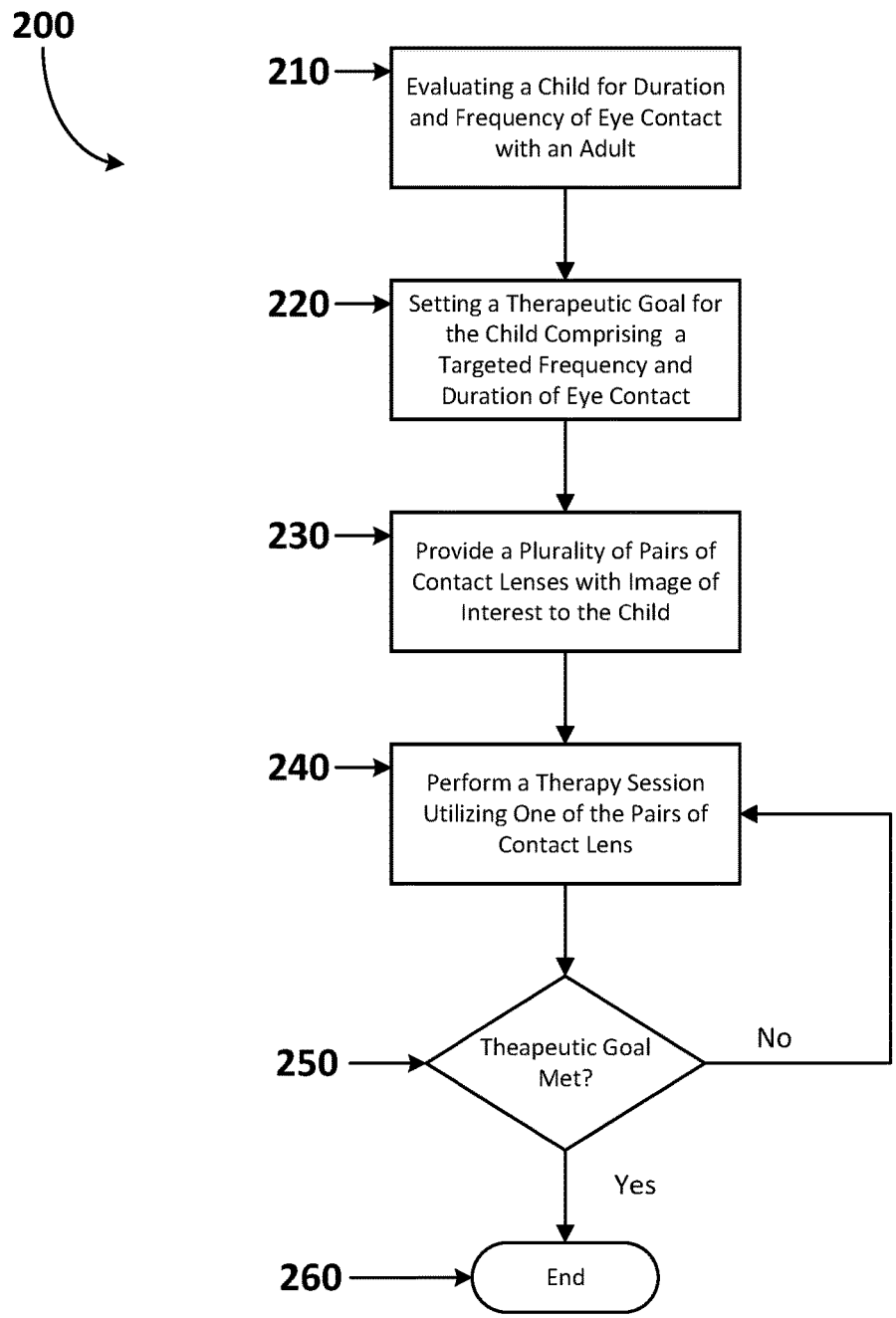
FIG. 2 illustrates an embodiment of an ASD treatment methodology in accordance with the present disclosure.

FIG. 2 illustrates an embodiment of an ASD treatment methodology 200 in accordance with the present disclosure that utilizes such a set of contact lenses.

In step 210 of the methodology, a child having ASD is evaluated for duration and frequency of eye contact with an adult. As described above, children having ASD have a significantly decreased eye contact compared to children without ASD. This establishes a baseline from which progress during therapy is judged.

In step 220 of the methodology, a therapeutic goal is set for the child, where the therapeutic goal comprises a targeted frequency and duration of eye contact. The therapeutic goal represents the point at which treatment using this methodology ends.

In step 230 of the methodology, a plurality of pairs of contact lenses having an image of interest to the child is provided to an adult who will be interacting with the child while using the contact lenses. The contact lenses are fit to the designated therapist who will work with the child on a daily basis. The same contact lenses can also be fit to the parent that has the most interaction with the child.

In an exemplary set of contact lenses, one subset of the set of lenses has the image of a subject of interest at an intensity of 80%, another subset has the image at an intensity of 50%, and another subset has the image in an intensity of 30%, and another subset has no image.

Alternatively, electronic contact lens capable of displaying an image downloaded to the contact lens could also be utilized. For example, bionic contact lenses could be used. Bionic contact lenses provide a virtual display have a variety of uses from assisting the visually impaired to the video game industry. Such devices have the form of a conventional contact lens with added bionics technology in the form of augmented reality with functional electronic circuits and infrared to create a virtual display, Smart contact lenses, such as those under development by Google could be used. Additionally, or alternatively, any type of electronic contact lens now known or later to be developed in the art, that is capable of displaying an image in varying degrees of intensity could be used.

In other embodiments, each of the pair of contact lenses could have a different image. In other embodiments, only one of the pair of contact lenses has an image. In other embodiments, rather than fading the image, half an image is presented. In various embodiments, the images may be brightly colored, and the color may vary between sets of contact lenses. In various other embodiments, the image may present text, such as, for example, the child's name In step 240 of the methodology, therapy session is performed wherein an adult interacting with the child during the therapy session utilizes one of the pair of contact lenses. A therapist trained in applied behavioral analysis will work with the child with a specific goal of improving eye contact. Therapy utilizing the contact lenses and applied behavioral analysis treatment will typically require 6 months to complete.

Figure 3:
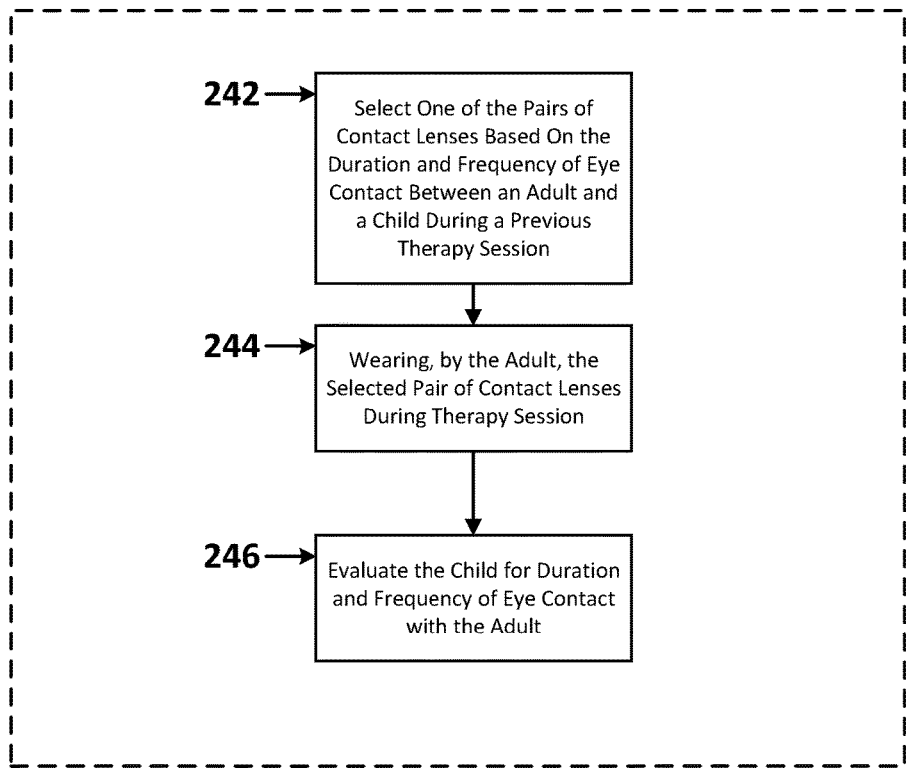
FIG. 3 illustrates a portion of the treatment methodology in FIG. 2 in greater detail.

Referring now to FIG. 3, FIG. 3 shows step 240 of the methodology in more detail.

In step 242 of the methodology, one of the pair of contact lenses is selected based on the duration and frequency of eye contact between the adult and the child during a previous therapy session.

In step 244 of the methodology, the adult wears selected pair of contact lenses during a therapy session.

In step 246 of the methodology, the adult evaluates the child for duration and frequency of eye contact during the therapy session.

In an exemplary use of such a set of contact lenses, a therapist or other person caring for a child with autism begins by wearing a pair of contact lenses that show the image at 80%. The person then attempts to interact with the child, noting the duration and frequency of eye contact by the child with the person during the interaction.

Over time, when the child's frequency and duration of eye contact with the therapist increases, the therapist then begins to wear another pair of contact lenses that has the image at a lower level of intensity. Over a period of treatment, the therapist, as the child continues to improve in duration and frequency of eye contact with therapist, where's contact lenses that show the image at a progressively lower and lower level of intensity.

During that period of treatment, parents and other caregivers may also wear contact lenses of the same degree of intensity as that used by the therapist. The ultimate goal is to improve the child's eye contact with caregivers and other persons who are not wearing contact lenses with images designed to attract the child's attention.

Referring back to FIG. 2, in step 250 of the methodology, it is then determined if the child's duration and frequency of eye contact meets the therapeutic goal set in step 220 of the methodology. If it does not, step 240 is repeated until the therapeutic goal is met. When the therapeutic goal is met, therapy utilizing the contact lenses can be terminated.

In the foregoing specification, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

The invention claimed is:

1. A method of promoting eye contact between an adult and a child with autism spectrum disorder comprising:
   providing a plurality of pairs of contact lenses, each of the plurality of pairs of contact lenses having an image depicting a subject of interest to the child, the image having an image intensity,
   evaluating the child, by the adult, in an initial therapy session,
   wherein a duration and a frequency of eye contact is measured during the initial therapy session;
   setting a therapeutic goal, by the adult, the therapeutic goal comprising a target duration and a target frequency of eye contact between the adult and the child;
   performing a plurality of therapy sessions until the duration and the frequency of eye contact between the adult and the child reaches the therapeutic goal, each of the plurality of sessions comprising the steps of:
   selecting one of the plurality of pairs of contact lenses based on the duration and a frequency of eye contact between the adult and the child;
   wearing, by the adult, the selected one of the plurality of pairs of contact lenses;
   interacting, by the adult, with the child,
   determining, by the adult, the duration and the frequency of eye contact between the adult and the child.

* * * * *